(12) United States Patent
Reckling et al.

(10) Patent No.: US 12,083,026 B2
(45) Date of Patent: Sep. 10, 2024

(54) SACRO-ILIAC JOINT STABILIZING IMPLANTS AND METHODS OF IMPLANTATION

(71) Applicant: SI-Bone Inc., Santa Clara, CA (US)

(72) Inventors: W. Carlton Reckling, Cheyenne, WY (US); Scott A. Yerby, Montara, CA (US); Paul M. Sand, Redwood City, CA (US)

(73) Assignee: SI-Bone Inc., Santa Clara, CA (US)

( * ) Notice: Subject to any disclaimer, the term of this patent is extended or adjusted under 35 U.S.C. 154(b) by 585 days.

(21) Appl. No.: 17/116,903

(22) Filed: Dec. 9, 2020

(65) Prior Publication Data

US 2021/0169660 A1   Jun. 10, 2021

Related U.S. Application Data

(60) Provisional application No. 62/945,653, filed on Dec. 9, 2019.

(51) Int. Cl.
*A61F 2/46* (2006.01)
*A61B 17/16* (2006.01)
(Continued)

(52) U.S. Cl.
CPC ........ *A61F 2/4611* (2013.01); *A61B 17/1662* (2013.01); *A61B 17/1739* (2013.01); *A61B 17/7055* (2013.01); *A61F 2/4603* (2013.01); *A61B 2017/564* (2013.01); *A61B 2090/376* (2016.02); *A61F 2002/30995* (2013.01); *A61F 2002/4687* (2013.01)

(58) Field of Classification Search
CPC .......... A61F 2/4611; A61F 2002/30995; A61F 2002/4687; A61B 17/7055
See application file for complete search history.

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

Follini et al.; U.S. Appl. No. 17/777,679 entitled "Rod coupling assemblies for bone stabilization constructs," filed May 18, 2022.
(Continued)

*Primary Examiner* — Julianna N Harvey
(74) *Attorney, Agent, or Firm* — Shay Glenn LLP

(57) ABSTRACT

Methods of implanting SI joint stabilization implants across a SI joint from a dorsal approach. The methods may include advancing an elongate implant positioning guide in a dorsal trajectory into an ilium of a subject, directly engaging a guide interface member of a SI joint stabilization implant with the positioning guide to restrict movement of the implant with respect to the positioning guide in at least one direction, and advancing the implant across the SI joint while guiding the implant with the positioning guide.

22 Claims, 10 Drawing Sheets

(51) Int. Cl.
*A61B 17/17* (2006.01)
*A61B 17/70* (2006.01)
A61B 17/56 (2006.01)
A61B 90/00 (2016.01)
A61F 2/30 (2006.01)

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,436,139 B1 | 8/2002 | Shapiro et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |

(56) References Cited

U.S. PATENT DOCUMENTS

| | | |
|---|---|---|
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 7,951,176 B2 | 5/2011 | Grady et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,257,398 B2 | 9/2012 | Jackson |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,398,682 B2 | 3/2013 | Jackson et al. |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,597,299 B2 | 12/2013 | Farr et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,808,298 B2 | 11/2017 | Stroncek et al. |

(56) References Cited

U.S. PATENT DOCUMENTS

| | | |
|---|---|---|
| 9,808,299 B2 | 11/2017 | Goel et al. |
| 9,808,337 B2 | 11/2017 | Housman et al. |
| 9,820,789 B2 | 11/2017 | Reiley |
| 9,826,986 B2 | 11/2017 | Donner et al. |
| 9,833,321 B2 | 12/2017 | Rindal et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| D816,843 S | 5/2018 | Lewis |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| D831,828 S | 10/2018 | Horton et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,188,442 B2 | 1/2019 | Mazel |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,841 B1 | 3/2019 | Compton et al. |
| 10,219,885 B2 | 3/2019 | Mamo et al. |
| D846,977 S | 4/2019 | Williams et al. |
| D847,336 S | 4/2019 | Asfora et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| D847,994 S | 5/2019 | Asfora et al. |
| 10,278,737 B2 | 5/2019 | Smith |
| 10,285,745 B2 | 5/2019 | Cummins et al. |
| 10,292,778 B2 | 5/2019 | Kostrzewski et al. |
| D850,616 S | 6/2019 | Asfora et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,335,217 B2 | 7/2019 | Lindner |
| 10,342,586 B2 | 7/2019 | Schneider |
| 10,349,983 B2 | 7/2019 | Purcell et al. |
| 10,349,986 B2 | 7/2019 | Wall et al. |
| 10,357,287 B2 | 7/2019 | Schlaepfer et al. |
| 10,363,070 B2 | 7/2019 | Jackson et al. |
| 10,363,073 B2 | 7/2019 | Raina et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,413,332 B2 | 9/2019 | Schumacher et al. |
| 10,426,533 B2 | 10/2019 | Mauldin et al. |
| 10,426,539 B2 | 10/2019 | Schifano et al. |
| 10,433,880 B2 | 10/2019 | Donner et al. |
| 10,456,268 B2 | 10/2019 | Mercier et al. |
| 10,463,402 B2 | 11/2019 | Biester et al. |
| 10,478,227 B2 | 11/2019 | Leff et al. |
| 10,485,596 B2 | 11/2019 | Koller et al. |
| 10,492,841 B2 | 12/2019 | Hartdegen et al. |
| 10,492,921 B2 | 12/2019 | McShane, III et al. |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| D875,931 S | 2/2020 | Asfora et al. |
| 10,555,758 B2 | 2/2020 | Magee et al. |
| 10,588,676 B2 | 3/2020 | Kang et al. |
| 10,588,677 B2 | 3/2020 | McDonnell |
| 10,595,917 B2 | 3/2020 | Loftus |
| 10,596,003 B2 | 3/2020 | Donner et al. |
| 10,603,054 B2 | 3/2020 | Asfora et al. |
| 10,603,055 B2 | 3/2020 | Donner et al. |
| 10,603,087 B2 | 3/2020 | Brenzel et al. |
| 10,603,176 B2 | 3/2020 | Arnold et al. |
| 10,610,275 B2 | 4/2020 | Brianza |
| 10,610,276 B2 | 4/2020 | Lutz |
| 10,610,370 B2 | 4/2020 | Baynham |
| 10,610,728 B2 | 4/2020 | Fano et al. |
| 10,617,453 B2 | 4/2020 | Beckett et al. |
| 10,653,454 B2 | 5/2020 | Frey et al. |
| 10,653,455 B2 | 5/2020 | Lehman et al. |
| 10,653,544 B2 | 5/2020 | Forsell |
| 10,660,657 B2 | 5/2020 | Slobitker et al. |
| 10,660,679 B2 | 5/2020 | Kang et al. |
| 10,660,684 B2 | 5/2020 | Kang et al. |
| 10,667,923 B2 | 6/2020 | Sullivan et al. |
| 10,682,131 B2 | 6/2020 | Fallin et al. |
| 10,682,150 B2 | 6/2020 | Stark |
| 10,682,437 B2 | 6/2020 | Roth |
| 10,709,570 B2 | 7/2020 | Stauffer et al. |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,792,074 B2 | 10/2020 | Jackson |
| 10,799,277 B2 | 10/2020 | Kulper et al. |
| 10,799,367 B2 | 10/2020 | Vrionis et al. |
| 10,806,597 B2 | 10/2020 | Sournac et al. |
| 10,842,511 B2 | 11/2020 | Patel et al. |
| 10,842,634 B2 | 11/2020 | Pasini et al. |
| D904,615 S | 12/2020 | Asfora et al. |
| D905,232 S | 12/2020 | Schifano et al. |
| 10,856,922 B2 | 12/2020 | Loke et al. |
| 10,864,029 B2 | 12/2020 | Redmond et al. |
| 10,898,333 B2 | 1/2021 | Cordaro |
| 10,905,472 B2 | 2/2021 | Mari et al. |
| 10,912,654 B2 | 2/2021 | Scheland |
| 10,932,838 B2 | 3/2021 | Mehl et al. |
| 10,939,944 B2 | 3/2021 | Wapner et al. |
| 10,940,008 B2 | 3/2021 | Patel |
| 10,959,830 B2 | 3/2021 | Williams et al. |
| 10,987,142 B2 | 4/2021 | Poelstra et al. |
| 10,993,754 B2 | 5/2021 | Kuntz et al. |
| 10,993,757 B2 | 5/2021 | Schifano et al. |
| 11,006,985 B2 | 5/2021 | Caploon et al. |
| D921,898 S | 6/2021 | Schifano et al. |
| D922,568 S | 6/2021 | Schifano et al. |
| 11,020,129 B2 | 6/2021 | LaNeve et al. |
| 11,033,309 B2 | 6/2021 | Zadeh |
| 11,052,229 B2 | 7/2021 | Althoff et al. |
| 11,058,443 B2 | 7/2021 | Siccardi et al. |
| 11,058,550 B2 | 7/2021 | LaNeve et al. |
| 11,058,556 B2 | 7/2021 | LaNeve et al. |
| D927,295 S | 8/2021 | Lanois |
| 11,116,557 B2 | 9/2021 | Zander et al. |
| 11,147,591 B2 | 10/2021 | Jackson |
| 11,147,597 B2 | 10/2021 | Jackson |
| 11,154,402 B1 | 10/2021 | LaNeve et al. |
| D935,025 S | 11/2021 | Schifano et al. |
| D935,876 S | 11/2021 | Lanois |
| 11,166,821 B2 | 11/2021 | Sazy |
| 11,172,939 B2 | 11/2021 | Donner et al. |
| 11,172,969 B2 | 11/2021 | Suddaby |
| 11,219,534 B2 | 1/2022 | Wall |
| 11,224,467 B2 | 1/2022 | Peterson et al. |

(56) References Cited

U.S. PATENT DOCUMENTS

| | | |
|---|---|---|
| 11,224,490 B2 | 1/2022 | MacMillan et al. |
| 11,259,854 B2 | 3/2022 | Thornes et al. |
| 11,266,767 B2 | 3/2022 | Roth et al. |
| 11,273,043 B1 | 3/2022 | Abbasi |
| 11,284,798 B2 | 3/2022 | Donner et al. |
| 11,284,887 B2 | 3/2022 | Hartdegen et al. |
| 11,298,747 B2 | 4/2022 | Klein et al. |
| D951,455 S | 5/2022 | Ginn |
| 11,318,020 B2 | 5/2022 | Bohl |
| 11,382,755 B2 | 7/2022 | LaNeve et al. |
| 11,382,770 B2 | 7/2022 | LaNeve et al. |
| 11,389,305 B2 | 7/2022 | LaNeve et al. |
| 11,413,073 B2 | 8/2022 | Castro |
| 11,419,652 B2 | 8/2022 | Wickham et al. |
| 11,419,653 B2 | 8/2022 | Castro |
| 11,419,654 B2 | 8/2022 | Castro |
| 11,432,829 B2 | 9/2022 | Castro |
| 11,452,548 B2 | 9/2022 | Harshman et al. |
| 11,510,801 B2 | 11/2022 | Archbold |
| D972,137 S | 12/2022 | Schifano et al. |
| 11,517,361 B2 | 12/2022 | Major et al. |
| 11,553,945 B2 | 1/2023 | Castro |
| 11,553,953 B1 | 1/2023 | Robbins |
| 11,580,268 B2 | 2/2023 | Suddaby |
| 11,583,326 B2 | 2/2023 | Suddaby |
| 11,607,251 B2 | 3/2023 | Albert et al. |
| 11,607,256 B1 | 3/2023 | Folsom et al. |
| 11,660,126 B1 | 5/2023 | Abbasi et al. |
| 11,850,156 B2 | 12/2023 | Mauldin et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Mamay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0071004 A1 | 3/2005 | Re et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1 | 1/2006 | Easley et al. |
| 2006/0025771 A1 | 2/2006 | Jackson |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089644 A1 | 4/2006 | Felix |
| 2006/0089656 A1 | 4/2006 | Allard et al. |
| 2006/0095038 A1 | 5/2006 | Jackson |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |

(56) References Cited

U.S. PATENT DOCUMENTS

| | | |
|---|---|---|
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0161927 A1 | 7/2008 | Savage et al. |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0171394 A1 | 7/2009 | Abdou |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0009966 A1 | 1/2011 | Michelson |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083883 A1* | 4/2012 | Ginn ............... A61B 17/1604 623/17.11 |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |

(56) References Cited

U.S. PATENT DOCUMENTS

| | | |
|---|---|---|
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0012384 A1 | 1/2014 | Kana et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1* | 12/2015 | Donner ............... A61B 17/84 600/595 |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0016630 A1 | 6/2016 | Papangelou et al. |
| 2016/0157908 A1 | 6/2016 | Cawley et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2017/0348034 A1 | 12/2017 | LaPierre et al. |
| 2017/0360570 A1 | 12/2017 | Berndt et al. |
| 2018/0008256 A1 | 1/2018 | Fallin et al. |
| 2018/0036041 A1 | 2/2018 | Pham et al. |
| 2018/0042652 A1 | 2/2018 | Mari et al. |
| 2018/0042735 A1 | 2/2018 | Schell et al. |
| 2018/0104063 A1 | 4/2018 | Asaad |
| 2018/0104068 A1 | 4/2018 | Sack |
| 2018/0104071 A1 | 4/2018 | Reckling et al. |
| 2018/0110624 A1 | 4/2018 | Amone |
| 2018/0110626 A1 | 4/2018 | McShane, III et al. |
| 2018/0177534 A1 | 6/2018 | Mesiwala et al. |
| 2018/0200063 A1 | 7/2018 | Kahmer et al. |
| 2018/0214192 A1 | 8/2018 | Roby et al. |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0235643 A1 | 8/2018 | Lins et al. |
| 2018/0243097 A1 | 8/2018 | Jones et al. |
| 2018/0256232 A1 | 9/2018 | Russell |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0289504 A1 | 10/2018 | Arthurs et al. |
| 2018/0296227 A1 | 10/2018 | Meek et al. |
| 2018/0296347 A1 | 10/2018 | Hamzey et al. |
| 2018/0296363 A1 | 10/2018 | Berry |
| 2018/0303520 A1 | 10/2018 | Rajpal |
| 2018/0303623 A1 | 10/2018 | Shoshtaev |
| 2018/0303624 A1 | 10/2018 | Shoshtaev |

(56) References Cited

U.S. PATENT DOCUMENTS

| | | |
|---|---|---|
| 2018/0317971 A1 | 11/2018 | Prevost |
| 2018/0360512 A1 | 12/2018 | Mari |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0046684 A1 | 2/2019 | Roth |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0090888 A1 | 3/2019 | Sand et al. |
| 2019/0091027 A1 | 3/2019 | Asaad et al. |
| 2019/0117827 A1 | 4/2019 | Roth |
| 2019/0125371 A1 | 5/2019 | Asfora et al. |
| 2019/0125408 A1 | 5/2019 | Asfora et al. |
| 2019/0133613 A1 | 5/2019 | Reiley et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0159818 A1 | 5/2019 | Schneider et al. |
| 2019/0159901 A1 | 5/2019 | Mauldin et al. |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0247094 A1 | 8/2019 | Yacoub et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1 | 10/2019 | Lindsey et al. |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |
| 2019/0343641 A1 | 11/2019 | Mauldin et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388228 A1 | 12/2019 | Donner et al. |
| 2019/0388242 A1 | 12/2019 | Harris et al. |
| 2020/0000595 A1 | 1/2020 | Jones et al. |
| 2020/0008817 A1 | 1/2020 | Reiley et al. |
| 2020/0008850 A1 | 1/2020 | Mauldin et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0069431 A1 | 3/2020 | Boehm et al. |
| 2020/0093603 A1 | 3/2020 | Manwill et al. |
| 2020/0100822 A1 | 4/2020 | Lipow |
| 2020/0129214 A1 | 4/2020 | Pepper et al. |
| 2020/0138485 A1 | 5/2020 | Kuwamura et al. |
| 2020/0138492 A1 | 5/2020 | Kavanagh |
| 2020/0146721 A1 | 5/2020 | Sadiq |
| 2020/0149137 A1 | 5/2020 | Roth |
| 2020/0170679 A1 | 6/2020 | Sciubba et al. |
| 2020/0206390 A1 | 7/2020 | Roth |
| 2020/0222088 A1 | 7/2020 | Kraus |
| 2020/0222195 A1 | 7/2020 | Assell et al. |
| 2020/0246158 A1 | 8/2020 | Bergey |
| 2020/0254140 A1 | 8/2020 | Roth |
| 2020/0261240 A1 | 8/2020 | Mesiwala et al. |
| 2020/0268449 A1 | 8/2020 | Solitro et al. |
| 2020/0268518 A1 | 8/2020 | Suh et al. |
| 2020/0268525 A1 | 8/2020 | Mesiwala et al. |
| 2020/0276019 A1 | 9/2020 | Shetty et al. |
| 2020/0281729 A1 | 9/2020 | Schifano et al. |
| 2020/0297496 A1 | 9/2020 | Mullin |
| 2020/0305896 A1 | 10/2020 | Castro |
| 2020/0315647 A1 | 10/2020 | Fojtik et al. |
| 2020/0315666 A1 | 10/2020 | Nichols et al. |
| 2020/0315669 A1 | 10/2020 | Dejardin |
| 2020/0323563 A1 | 10/2020 | Rezach et al. |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0022882 A1 | 1/2021 | Dang et al. |
| 2021/0085470 A1 | 3/2021 | Ty |
| 2021/0107093 A1 | 4/2021 | Tempco |
| 2021/0196332 A1 | 7/2021 | Patel |
| 2021/0212833 A1 | 7/2021 | Chin et al. |
| 2021/0228360 A1 | 7/2021 | Hunt et al. |
| 2021/0228363 A1 | 7/2021 | Suddaby |
| 2021/0236146 A1 | 8/2021 | Donner et al. |
| 2021/0244449 A1 | 8/2021 | Castro |
| 2021/0244452 A1 | 8/2021 | Castro |
| 2021/0275233 A1 | 9/2021 | Fang et al. |
| 2021/0338454 A1 | 11/2021 | Afzal |
| 2021/0346038 A1 | 11/2021 | Fiechter et al. |
| 2021/0353337 A1 | 11/2021 | Kaufmann et al. |
| 2021/0353338 A1 | 11/2021 | Meek et al. |
| 2021/0393298 A1 | 12/2021 | Castro |
| 2021/0393408 A1 | 12/2021 | Ginn |
| 2021/0393409 A1 | 12/2021 | Ginn |
| 2022/0031365 A1 | 2/2022 | Suh et al. |
| 2022/0031474 A1 | 2/2022 | Reckling et al. |
| 2022/0151668 A1 | 5/2022 | Mauldin et al. |
| 2022/0273446 A1 | 9/2022 | Stuart et al. |
| 2022/0273447 A1 | 9/2022 | Ginn |
| 2022/0273448 A1 | 9/2022 | Ginn et al. |
| 2022/0280303 A1 | 9/2022 | Mauldin et al. |
| 2022/0296377 A1 | 9/2022 | Ginn et al. |
| 2022/0296378 A1 | 9/2022 | Ginn |
| 2022/0304672 A1 | 9/2022 | Kalhorn et al. |
| 2022/0304813 A1 | 9/2022 | Ginn et al. |
| 2022/0304814 A1 | 9/2022 | Ginn |
| 2022/0361924 A1 | 11/2022 | Castro |
| 2022/0409381 A1 | 12/2022 | Ginn |
| 2023/0000630 A1 | 1/2023 | Ginn et al. |
| 2023/0000631 A1 | 1/2023 | Ginn et al. |
| 2023/0076180 A1 | 3/2023 | Schifano et al. |
| 2023/0088477 A1 | 3/2023 | Roussouly et al. |
| 2023/0145974 A1 | 5/2023 | Asfora |
| 2023/0263554 A1 | 8/2023 | Stuart et al. |
| 2023/0270559 A1 | 8/2023 | Mesiwala et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| CN | 104968283 A | 10/2015 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3484387 A1 | 5/2019 |
| EP | 3501457 A1 | 6/2019 |
| EP | 3593745 A2 | 1/2020 |
| EP | 3616634 A1 | 3/2020 |
| EP | 3661441 A1 | 6/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |

(56) References Cited

FOREIGN PATENT DOCUMENTS

| | | |
|---|---|---|
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009000501 A | 1/2009 |
| JP | 2009521990 A | 6/2009 |
| JP | 2009533159 A | 9/2009 |
| JP | 2010137016 A | 6/2010 |
| JP | 2012030105 A | 2/2012 |
| JP | 2014000402 A | 1/2014 |
| JP | 2015510506 A | 4/2015 |
| JP | 2017528251 A | 9/2017 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2006/116850 A1 | 11/2006 |
| WO | WO2009/025884 A2 | 2/2009 |
| WO | WO2009/029074 A1 | 3/2009 |
| WO | WO2010/105196 A1 | 9/2010 |
| WO | WO2011010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2012/048008 A1 | 4/2012 |
| WO | WO2013/000071 A1 | 1/2013 |
| WO | WO2013/052807 A2 | 4/2013 |
| WO | WO2013/119907 A1 | 8/2013 |
| WO | WO2014/145902 A1 | 9/2014 |
| WO | WO2017/147140 A1 | 8/2017 |
| WO | WO2017/147537 A1 | 8/2017 |
| WO | WO2019/152737 A1 | 8/2019 |
| WO | WO2020/168269 A1 | 8/2020 |
| WO | WO2021/102429 | 5/2021 |
| WO | WO2022/125619 A1 | 6/2022 |

OTHER PUBLICATIONS

Stuart et al.; U.S. Appl. No. 17/812,945 entitled "Sacro-iliac joint stabilizing implants and methods of implantation," filed Jul. 15, 2022.

Mauldin et al.; 17/805,165 entitled "Systems, device, and methods for joint fusion," filed Jun. 2, 2022.

Mesiwala et al.; U.S. Appl. No. 17/217,794 entitled "Implants for spinal fizzation or fusion," filed Mar. 20, 2021.

Acumed; Acutrak Headless Compressioin Screw (product information); 12 pgs; © 2005; retrieved Sep. 25, 2014 from http://www.rosed.ac.uk/fellows/lvanrensburg/classification/surgtech/acumed/manuals/acutrak-brochure%200311.pdf.

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Stuart et al.; U.S. Appl. No. 17/104,753 entitled "Bone stabilizing implants and methods of placement across SI joints," filed Nov. 25, 2020.

Sand et al.; U.S. Appl. No. 17/447,550 entitled "Systems and methods for decorticating the sacroloac joint," filed Sep. 13, 2021.

Lindsey et al.; U.S. Appl. No. 18/066,872 entitled "Threaded implants and methods of use across bone segments," filed Dec. 15, 2022.

Mauldin et al.; U.S. Appl. No. 17/822,360 entitled "Fenestrated implant," filed Aug. 25, 2022.

Mesiwala et al.; U.S. Appl. No. 17/649,265 entitled "Implants for spinal fixation and or fusion," filed Jan. 28, 2022.

Mesiwala et al.; U.S. Appl. No. 17/649,296 entitled "Implants for spinal fixation and or fusion," filed Jan. 28, 2022.

Mauldin et al.; U.S. Appl. No. 17/650,473 entitled "Fenestrated implant," filed Feb. 9, 2022.

Schneider et al.; U.S. Appl. No. 17/443,388 entitled "Matrix implant," filed Jul. 26, 2021.

Reiley et al.; U.S. Appl. No. 18/317,832 entitled "Implants for bone fixation or fusion," filed May 15, 2023.

Stuart et al.; U.S. Appl. No. 18/356,880 entitled "Sacro-iliac join stabilizing implants and methods of implantation," filed Jul. 21, 2023.

\* cited by examiner

SACRO-ILIAC JOINT STABILIZING IMPLANTS AND METHODS OF IMPLANTATION

CROSS REFERENCE TO RELATED APPLICATIONS

This application claims the benefit of priority of U.S. Application No. 62/945,653, filed Dec. 9, 2019, the entire disclosure of which is fully incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Implants may be positioned across a sacro-iliac ("SI") joint to help stabilize the joint. Regions of the ilium may have greater density than regions of the sacrum. Depending on one or more of the delivery trajectory, the target location for implantation, and the configuration of the implant, the differences in bone density may present challenges while advancing some SI joint implants across the SI joint. Implantation methods are needed that accommodate for the differences in bone density and can facilitate the successful delivery of the SI joint implant from a dorsal approach.

SUMMARY OF THE DISCLOSURE

One aspect of the disclosure is a method of positioning a SI joint stabilization implant across a SI joint from a dorsal approach. The method may include advancing an elongate implant positioning guide ("positioning guide," or "guide") in a dorsal trajectory into an ilium of a subject, engaging a guide interface member of a SI joint stabilization implant with the positioning guide to restrict movement of the implant with respect to the positioning guide in at least one direction, at a time subsequent to the engaging step, advancing the implant across the SI joint while guiding the implant with the positioning guide, and removing the positioning guide from the ilium.

In this aspect, the engaging step may limit the amount of implant migration towards the sacrum while advancing the implant across the SI joint.

In this aspect, advancing the positioning guide into an ilium may comprise advancing the positioning guide into the ilium between lateral and medial cortical walls of the ilium. In this aspect, advancing the positioning guide may comprise advancing the positioning guide only into the ilium.

In this aspect, the method may optionally further comprise, at a time subsequent to positioning the positioning guide into the ilium, advancing a sacrum positioning guide into a sacrum of the patient, engaging a second guide interface member of the implant with the sacrum positioning guide, wherein the implant advancing step occurs while also guiding the implant with the sacrum positioning guide, and removing the sacrum positioning guide from the sacrum. Engaging a second guide interface section of the implant with a sacrum positioning guide may occur prior to advancing a sacrum positioning guide into a sacrum of the patient. The method may further include advancing a second sacrum positioning guide in a dorsal trajectory or dorsal approach into the sacrum of a subject, and engaging a second sacrum guide interface member of the implant with the second sacrum positioning guide to restrict movement of the implant with respect to the second sacrum positioning guide in at least one direction.

In this aspect, the method may optionally further include, at a time prior to engaging the guide interface member with the positioning guide, engaging a sharpened broach with the positioning guide, and advancing the broach towards the SI joint to create a space for the implant while guiding the broach with the positioning guide, and removing the broach to allow dorsal access to the space.

In this aspect, engaging a guide interface member of the implant with the positioning guide may comprise positioning an annular member of the implant over a proximal region of the positioning guide.

In this aspect, engaging a guide interface member of the implant with the positioning guide may comprise positioning an arcuate member of the implant around a proximal region of the positioning guide.

In this aspect, the method may further comprise advancing a second ilium positioning guide in a dorsal trajectory into the ilium of a subject, and engaging a second guide interface member of the implant with the second ilium positioning guide to restrict movement of the implant with respect to the second ilium positioning guide in at least one direction.

One aspect of this disclosure is a method of implanting a SI joint implant across a SI joint from a dorsal approach while preventing the SI joint implant from migrating away from the ilium and towards the sacrum. This aspect may include any other method step or sequence of steps claimed and/or described herein. In this aspect, the preventing step may include engaging a positioning guide with a portion of the implant.

DETAILED DESCRIPTION

The disclosure herein is related to SI joint stabilizing implants and methods of implanting SI joint stabilizing implants across a SI joint. The methods include implanting a stabilizing implant from a dorsal approach across the SI joint with a first portion of the implant positioned in the ilium and a second portion of the implant positioned in the sacrum. The implants herein are sized and configured to be implanted according to any of the methods of implantation herein, unless indicated to the contrary.

Regions of the ilium into which a portion of the implant is positioned may have greater density than regions of the sacrum into which a second portion of the implant is positioned. When positioning a SI joint implant across a SI joint from a dorsal approach, the implant may tend to deflect away from denser cortical iliac bone and migrate towards and into the less dense sacrum, preventing proper positioning of the implant across the SI joint. Implantation methods and implants are described herein that can maintain proper implant trajectory when advancing the SI joint implant across the SI joint from a dorsal approach. The methods and approaches herein can account for the differences in bone density between the ilium and sacrum and prevent the implant from migrating away from denser iliac bone during implantation.

Figure 11A:
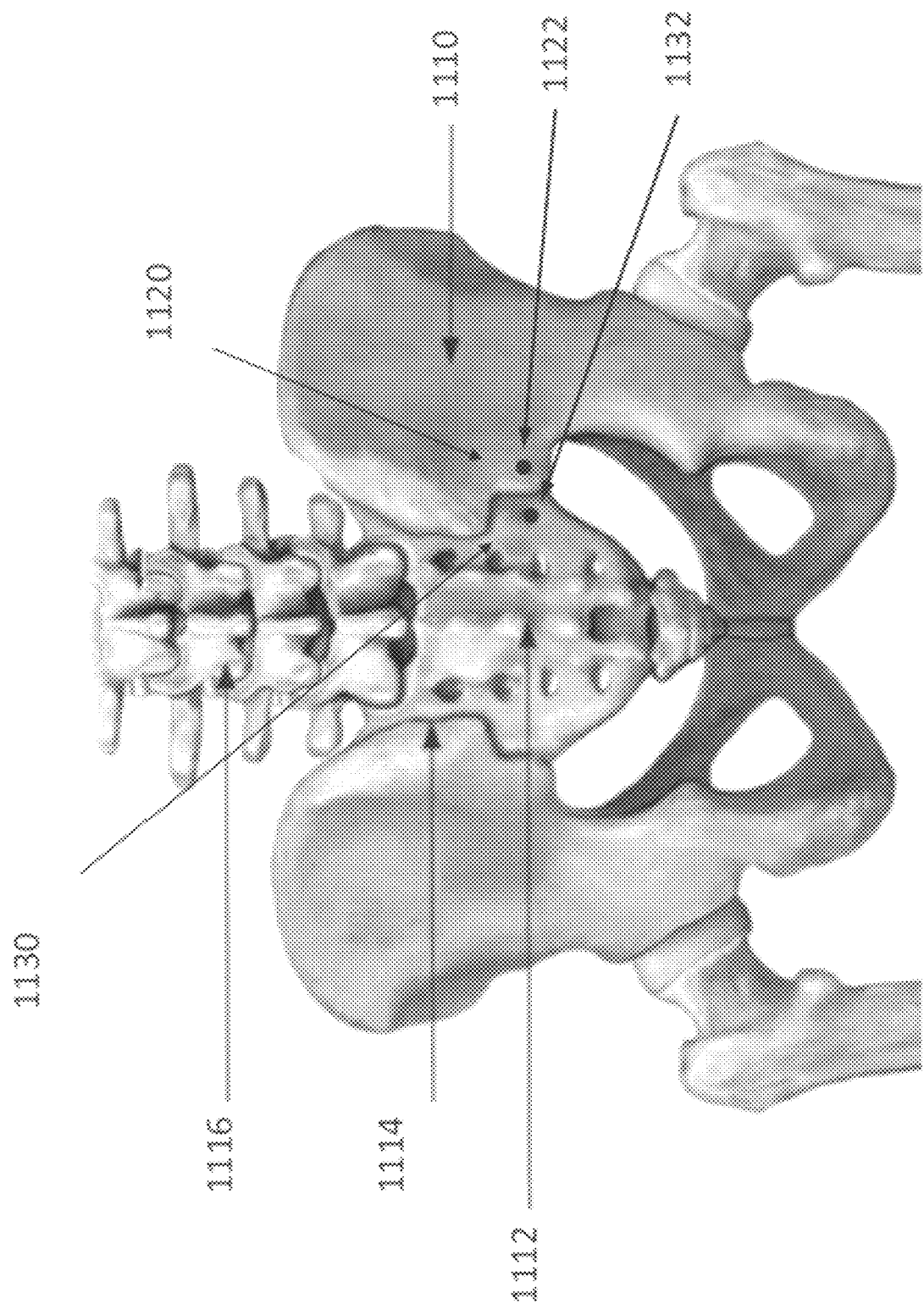
FIG. 11A illustrates a posterior view and exemplary locations for positioning guides.
Figure 11B:
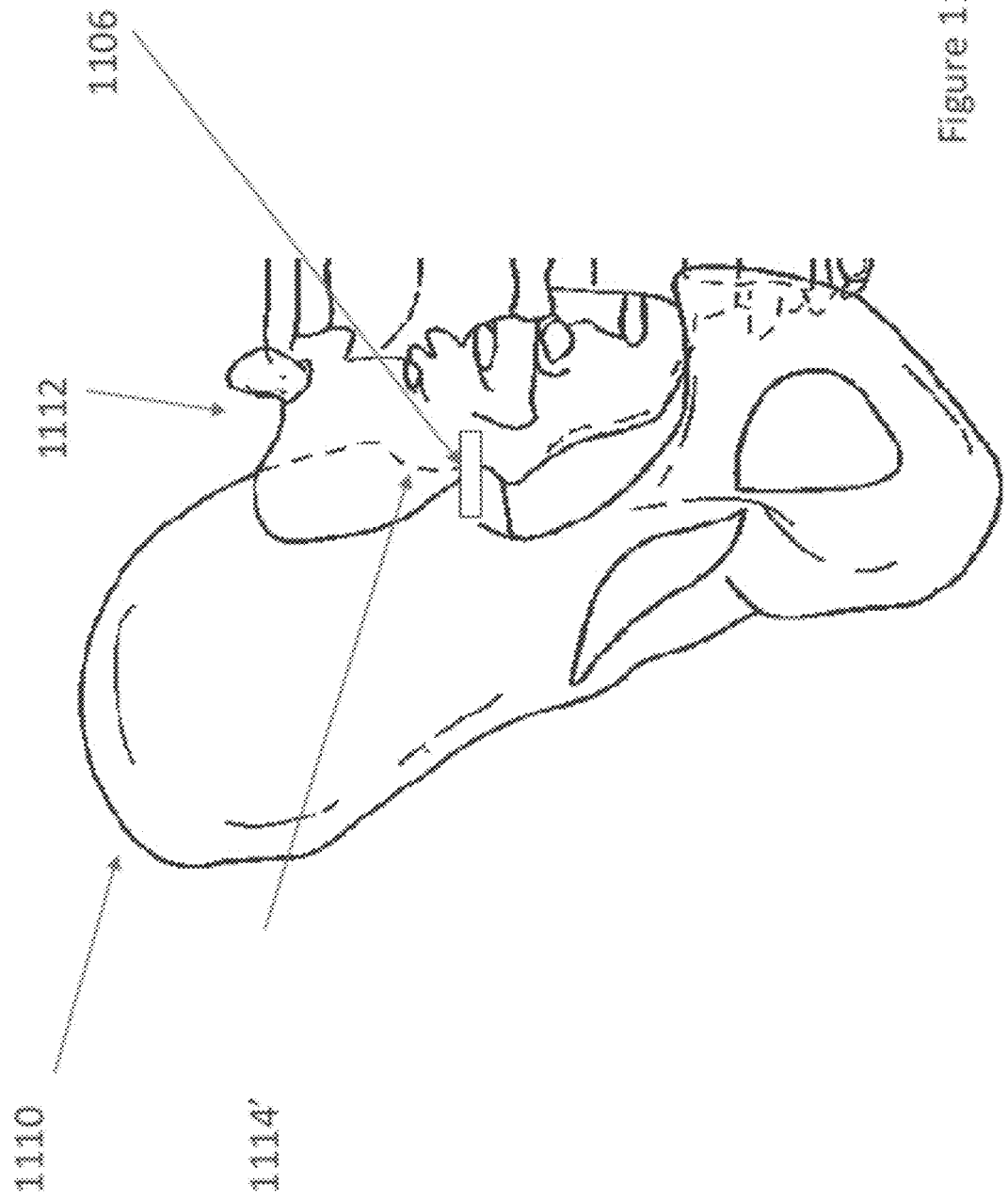
FIG. 11B illustrates an exemplary implantation location for a SI joint implant across a SI joint.

The methods herein may include advancing one or more positioning guides, any of which may be referred to herein as a "guide," into an ilium from a dorsal approach, and in some embodiments between lateral and medial cortical walls of the ilium. FIG. 11A illustrates a posterior view and a general dorsal approach for implanting the SI joints herein across the SI joint. FIG. 11B illustrates an exemplary implant 1106 implanted across a SI joint 1114' with a first region of the implant disposed in ilium 1110, a second region of the implant disposed in sacrum 1112, and a central region extending across the SI joint 1114'. FIGS. 11A and 11B, which are referenced in more detail below, illustrate ilium 1110, sacrum 1112, the SI joints 1114 and 1114', and lumbar vertebrae 1116. FIG. 11A also illustrates a general region 1120 for a starting point for advancing an ilium positioning guide into the ilium, and a general region 1130 for a starting point for advancing a sacrum positioning guide into the ilium. FIG. 11A further illustrates an exemplary ilium starting point 1122 for an ilium positioning guide, as well as an exemplary sacrum starting point 1132 for a sacrum positioning guide. Any of the ilium positioning guides herein may have a starting point in general region 1120, such as ilium starting point 1122. Any of the sacrum positioning guides herein may have a starting point in general region 1130, such as sacrum starting point 1132. A radiographic view image may be obtained and utilized to help guide the positioning guide into the ilium between lateral and medial cortical walls of the ilium, which are illustrated generally in FIGS. 11A and 11B. Methods herein include interfacing the ilium positioning guides herein with a portion of the SI joint implant, such as an interface member of the implant, to guide the implant across the SI joint. By positioning an ilium positioning guide in the relatively dense region of the ilium, and interfacing and engaging the positioning guide with the implant, the guide can help ensure a portion of the implant will stay on course during advancement during implantation in the dorsal approach, rather than migrating away from the relatively dense cortical ilium bone and towards the sacrum. The positioning guides herein thus interface directly with the implant and are sized and configured to act as a guide for a portion of the implant to ensure that the ilium portion of implant is properly positioned in the ilium and that the implant is properly implanted across the SI joint.

The positioning guides are sized and configured to generally restrict movement of the implant with respect to the positioning guide in at least one direction. The implant may be free to move relative to the positioning guide in other ways or directions. For example, once interfaced, the implant may still be able to rotate relative to the guide, such as in FIGS. 1A and 1B, but the guide can still maintain the desired trajectory of at least a portion of the implant when the implant is advanced in the dorsal trajectory over the guide.

The methods herein include advancing the implant across the SI joint, while the guide helps guide a portion of the implant into the ilium. The methods may also include removing the positioning guide from the ilium after the implant has been positioned across the SI joint.

The methods herein may include positioning more than one positioning guide, optionally more than one guide in the ilium, and optionally one or more guides into sacral bone. Any of the one or more guides herein may be sized and configured to function as a positioning guide to help guide a portion of the implant into ilium bone or sacral bone.

In some alternative methods and implants, it may be possible to advance a SI joint stabilizing implant from a dorsal approach across a SI joint without using a positioning guide. For example, these methods may include radiographically visualizing a teardrop view of the ilium and advancing the implant while visualizing the teardrop view to ensure a portion of the implant stays sufficiently on course into the teardrop region of the ilium. Any of the methods herein may thus optionally exclude an ilium positioning guide, and may rely on a radiographic image, such as a teardrop view, to help maintain a desired implant trajectory into a teardrop region of the ilium. Implants implanted according to these methods may be implanted with or without a broach (described in more detail below), and if implanted without the use of a broach, the implants may have distal end regions that are configured to penetrate into bone, optionally having sharpened distal ends.

The SI joint stabilizing implants herein, such as any of those shown in FIGS. 1A-10, are generally sized and configured to be able to interface with an elongate ilium positioning guide, and may be sized and configured to interface with one or more additional positioning guides, which may be ilium or sacral guides.

The following exemplary SI joint stabilizing implants may be used in any of the methods of SI joint stabilization herein. Even if the textual description of an embodiment does not expressly include it, it is understood that features shown in different embodiments may be incorporated together. For example, the implants shown in FIGS. 1A, 1B, 2A and 2B each have an interface member with an annular inner surface that defines a lumen, even if the text does not expressly include this description. Additionally, similar components may be similarly labeled in different embodiments. For example, it is understood that references to elements 10, 20, 30, 40, etc., in the figures may illustrate systems, even if the text related to any particular embodiment is silent with reference to a reference number shown in the figure.

Figure 1A:
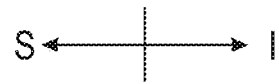
FIGS. 1A and 1B illustrate an exemplary SI joint implant engaged with a positioning guide.
Figure 1A:
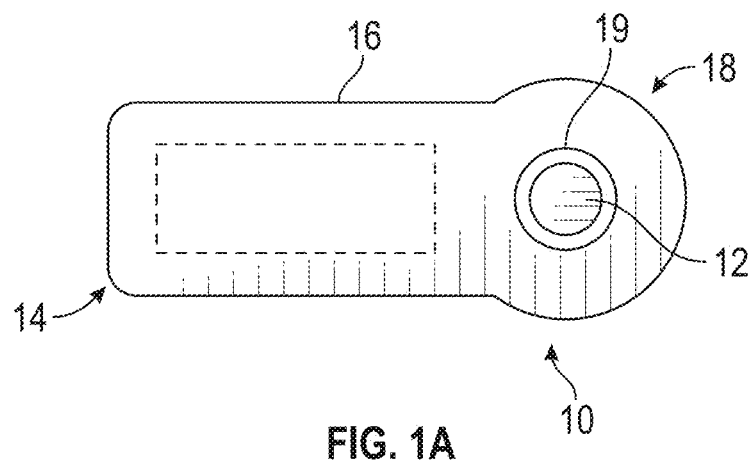
Figure 1B:
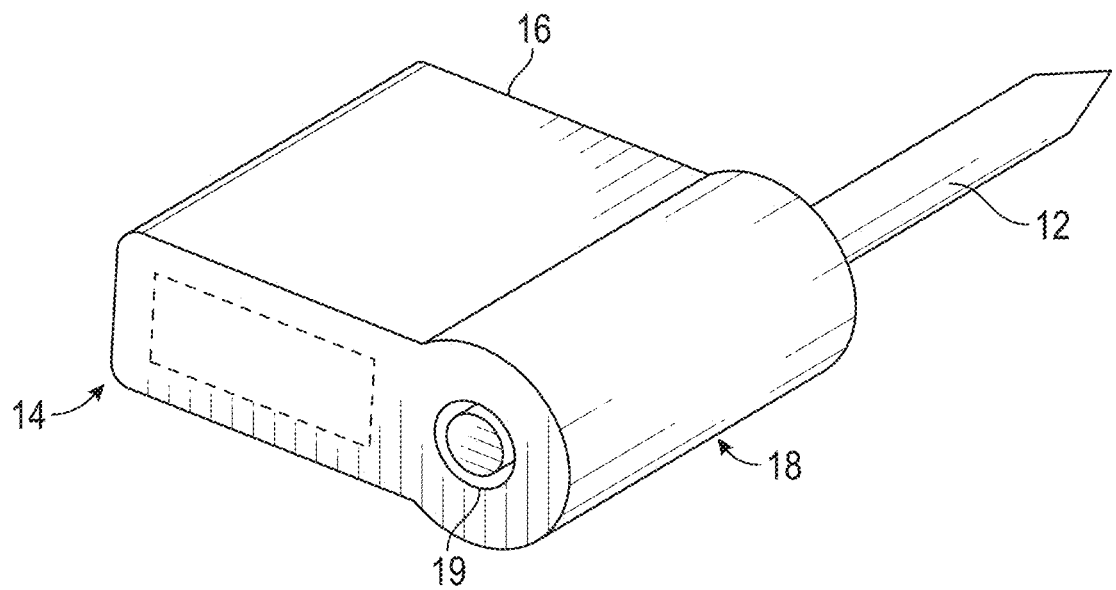

FIGS. 1A and 1B illustrate (dorsal view and perspective view, respectively) an exemplary system 10 that includes SI joint stabilizing implant 14 that includes an ilium guide interface member 18 interfacing, which may be also referred to herein as engaging, with elongate ilium guide 12. Implant 14 includes main body 16, a portion of which is disposed across the joint when the implanted is implanted. The interface member 18 includes a surface 19 that has a configuration, in this example annular, that is sized and configured to interface with the corresponding configuration of elongate ilium guide 12. In these figures, the guide may or may not already be positioned in an ilium, such as at the exemplary general location shown in FIG. 11. The interface between the guide and the interface member of the implant restricts the movement of the implant interface guide member with respect to the elongate ilium guide in one or more directions. In this example, implant may still be rotated relative to the guide. In this embodiment, the guide has a cylindrical configuration, with an annular outer profile in cross section along almost all of its length (except for the distal tip region, which may be configured to penetrate into bone). In figures herein, including FIGS. 1A and 10, "S" refers to sacrum, and "I" refers to ilium. Any of the guides herein may be considered to have a cylindrical configuration along all or substantially all of its length.

Figure 2A:
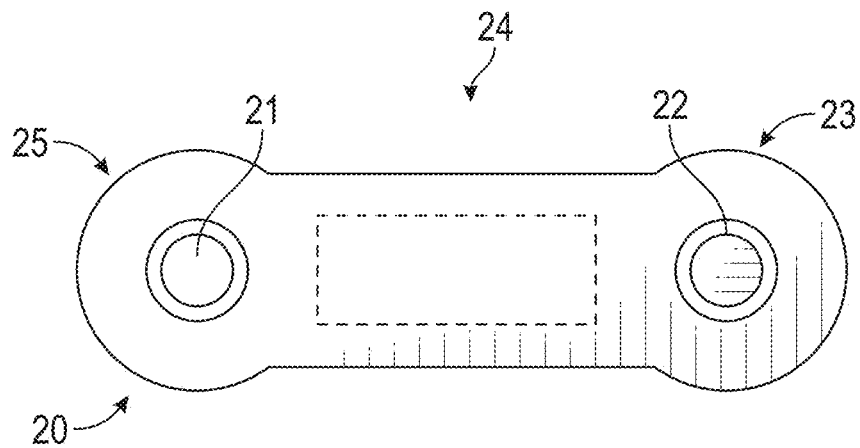
FIGS. 2A and 2B illustrate an exemplary SI joint implant engaged with first and second positioning guides.
Figure 2B:
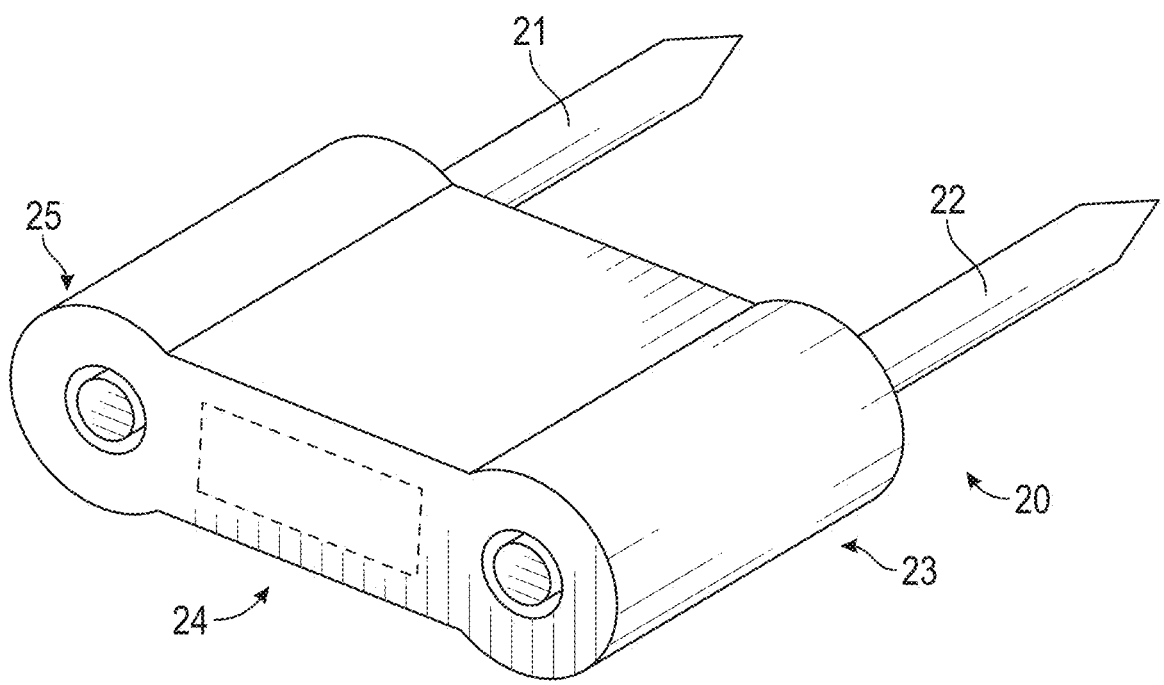
Figure 3A:
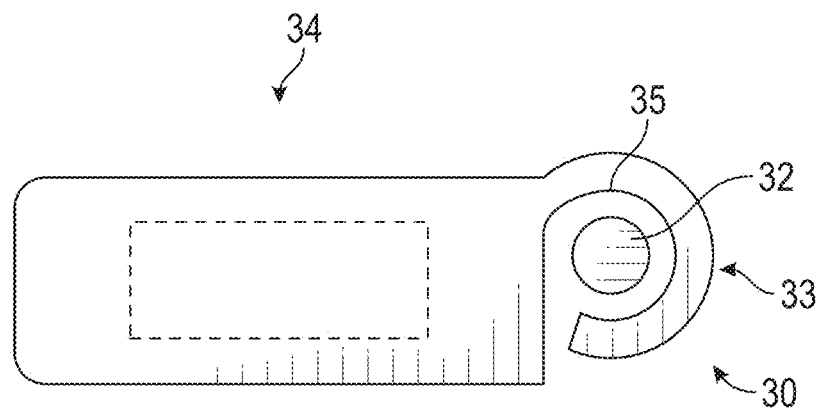
FIGS. 3A and 3B illustrate an exemplary SI joint implant engaged with a positioning guide.
Figure 3B:
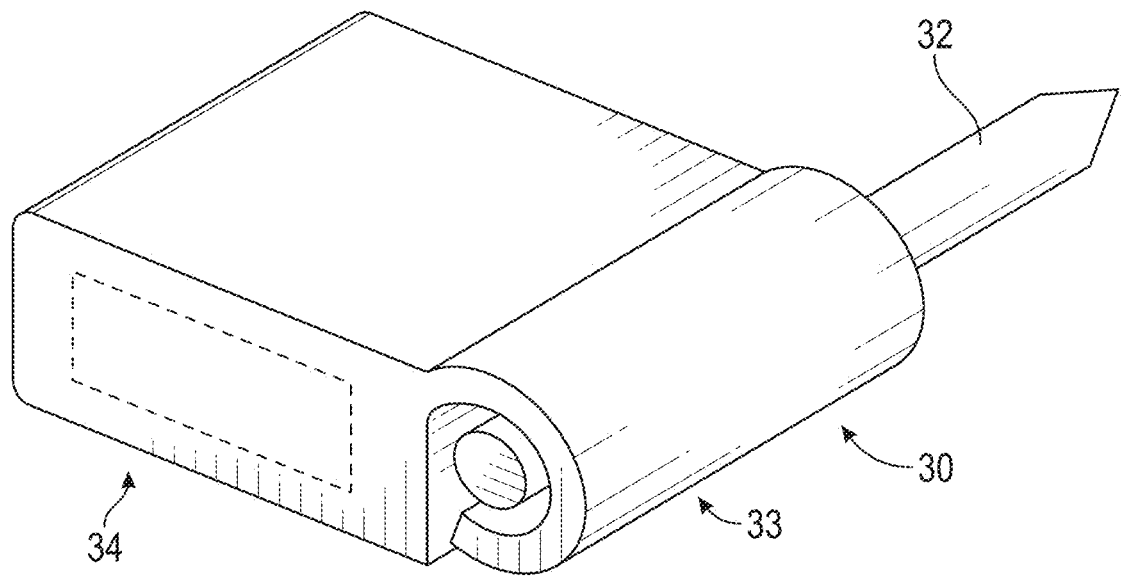

Any of the guides herein may include a sharpened or pointed distal end (e.g., as shown in FIGS. 1B, 2B, 3B, etc.) that may be configured to help penetrate into bone, such as iliac bone and/or sacral bone.

FIGS. 2A and 2B illustrate exemplary system 20 that includes SI joint stabilizing implant 24, ilium guide 22, and an optional elongate sacral guide 21. In the figures shown, the ilium guide 22 and the sacral guide 21 may or may not yet be positioned within the ilium and sacrum, respectively. In some methods, the one or more guides may be inserted into bone, and then the implant may be advanced over the guides. In some embodiments, the implant is interfaced with the one or more guides, and subsequently the one or more guides can be inserted into bone. Interfacing the implant to a plurality of guides (in examples with more than one guide) before guide insertion may help prevent the guides from being inserted into bone and spaced apart at positions that prevent the implant from then be interfaced with the guides and successfully advanced along the guides and across the SI joint. Interfacing the implant with the guides first may help the guides being properly spaced apart to accommodate the implant during implantation. In any embodiment herein, an ilium guide may be inserted into iliac bone, followed by interfacing the guide with the implant, followed by interfacing the implant with a sacrum guide, and followed by inserting the sacrum guide into a sacrum. The implant may then be advanced across the SI joint.

Any of the dashed lines herein (such as in FIGS. 1A, 2A, 3A and 4A) in an implant body can indicate an optional bore or opening within a main body portion of the implant, which may extend through distal and proximal implant body surfaces.

FIGS. 3A and 3B illustrate an exemplary system 30 that includes implant 34, which is configured to interface with guide 32. Implant 34 includes guide interface member 33 that has a surface 35 sized and configured to interface with guide 32, which may be an ilium guide. Member 33 is in this embodiment curvilinear and has an almost completely annular configuration.

Figure 4A:
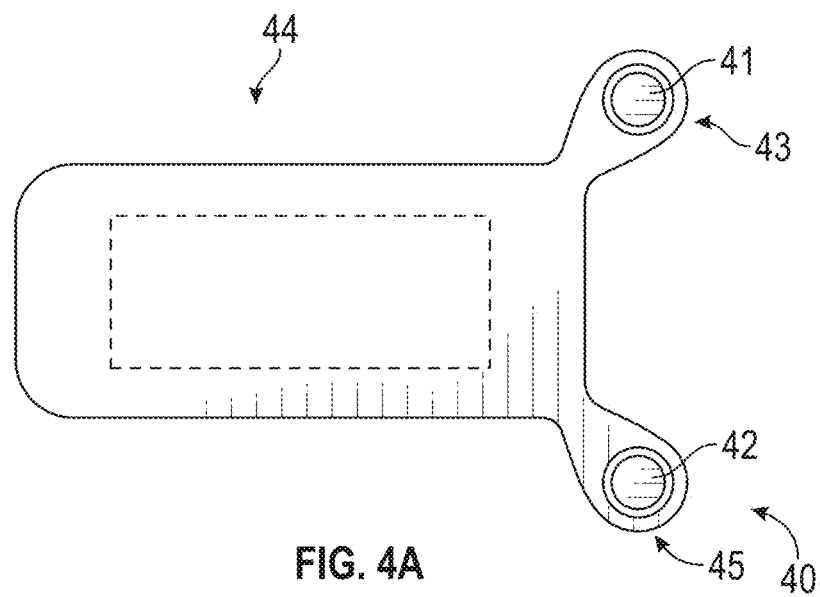
FIGS. 4A and 4B illustrate an exemplary SI joint implant engaged with first and second positioning guides.
Figure 4B:
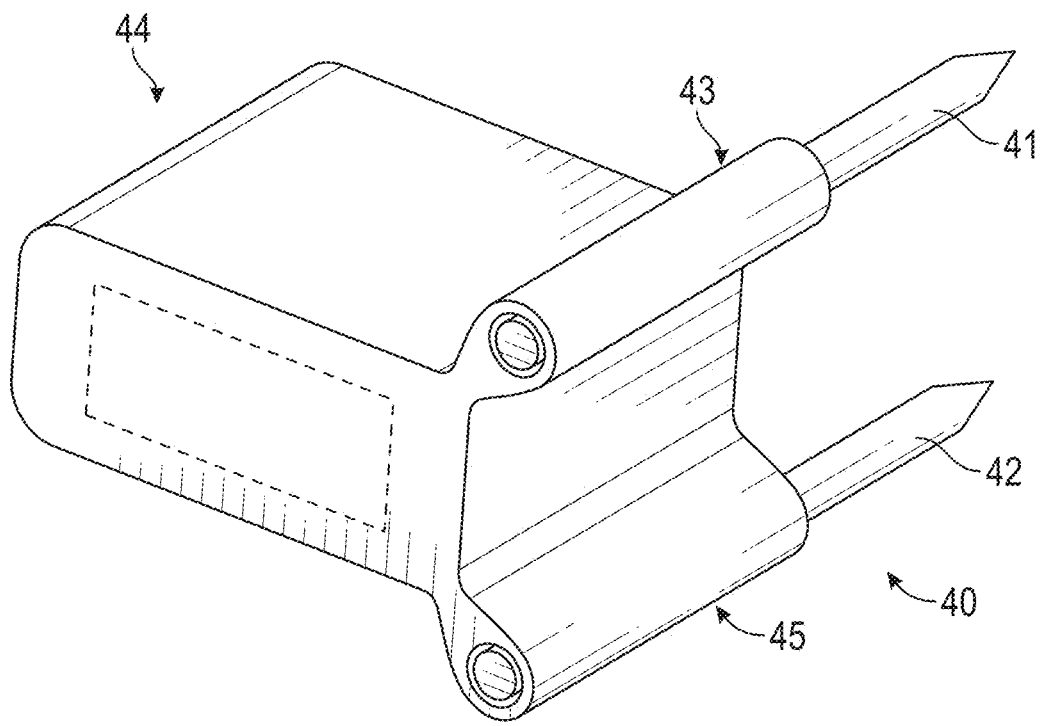

FIGS. 4A and 4B illustrate exemplary system 40 that includes implant 44 with first and second ilium guide interface members 43 and 45, each of which has a surface configured to interface with guide 41 and guide 42, respectively. Members 43 and 45 in this embodiment extend away from the main body region further than the guide interface members in FIGS. 1A, 1B, 2A and 2B, for example.

Figure 5A:
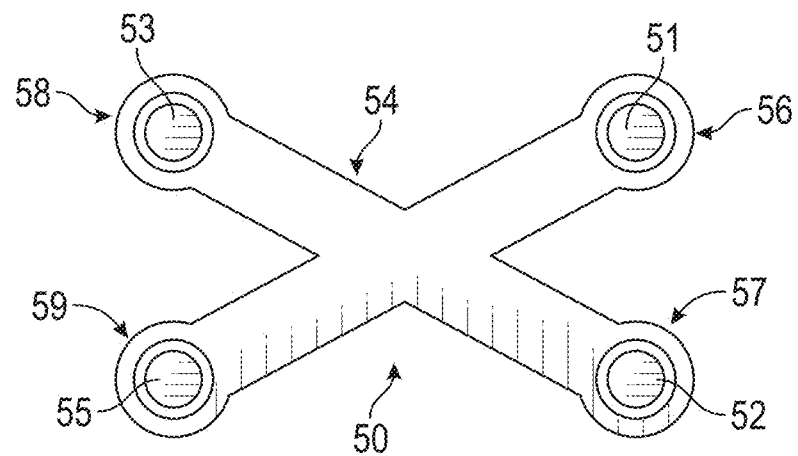
FIGS. 5A and 5B illustrate an exemplary SI joint implant engaged with a plurality of positioning guides.
Figure 5B:
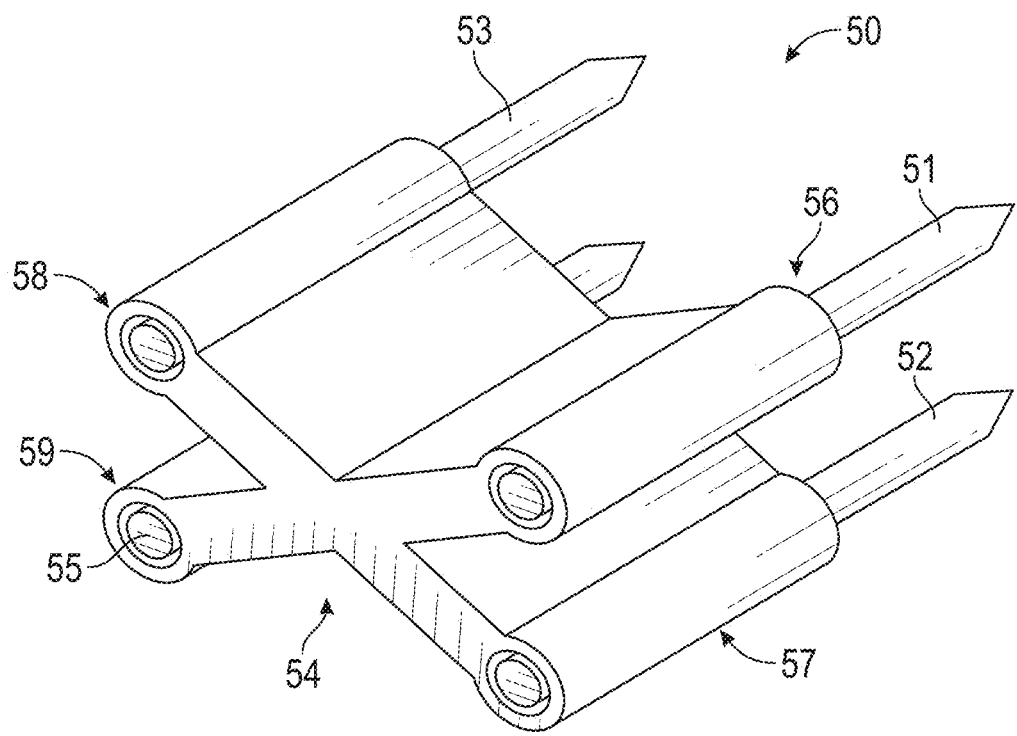

FIGS. 5A and 5B illustrate an exemplary system 50 that includes exemplary implant 54, and exemplary ilium guides 51 and 52 and sacral guides 53 and 55. Implant 50 includes four guide members 56, 57, 58 and 59, each configured to interface with a separate guide. The implant main body has a general "X" or crossing configuration, but could have other main body configurations, such as square, rectangular, oval, etc., and may still have four (or more) guide interface members.

Figure 6A:
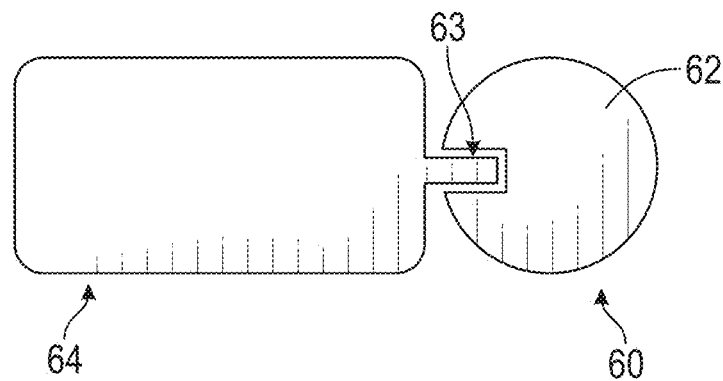
FIGS. 6A and 6B illustrate an exemplary SI joint implant engaged with a positioning guide.
Figure 6B:
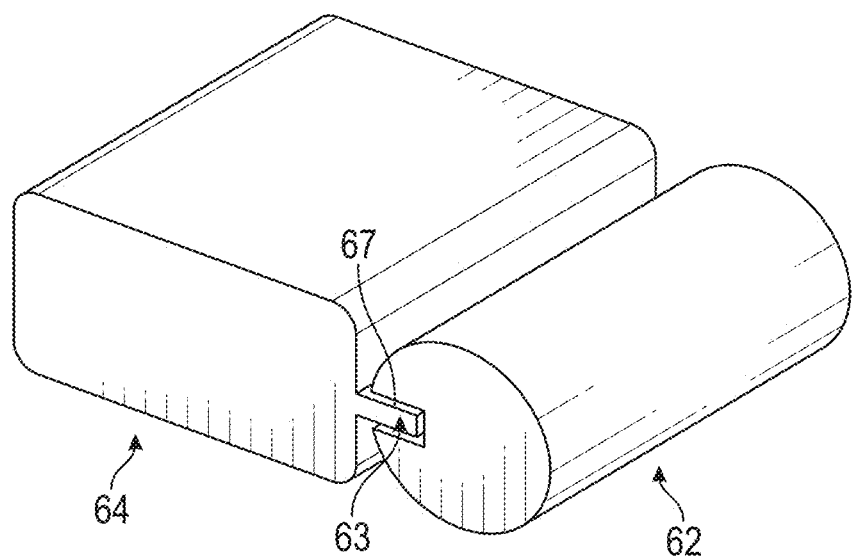

FIGS. 6A and 6B illustrate an exemplary system 60 that includes implant 64 configured to interface with guide 62. In this embodiment guide 62 includes a recessed region that is configured to stably interface with interface member 63 that in this example is a protrusion or extension from a main body region of the implant. This is an example of the implant having a guide interface member that extends within the guide, compared with guide interface members that extend around a portion of the guide, such as in FIGS. 1A-5B. The interface in this embodiment causes guide 62 to act as a guide for implant 64 during implantation.

Figure 7:
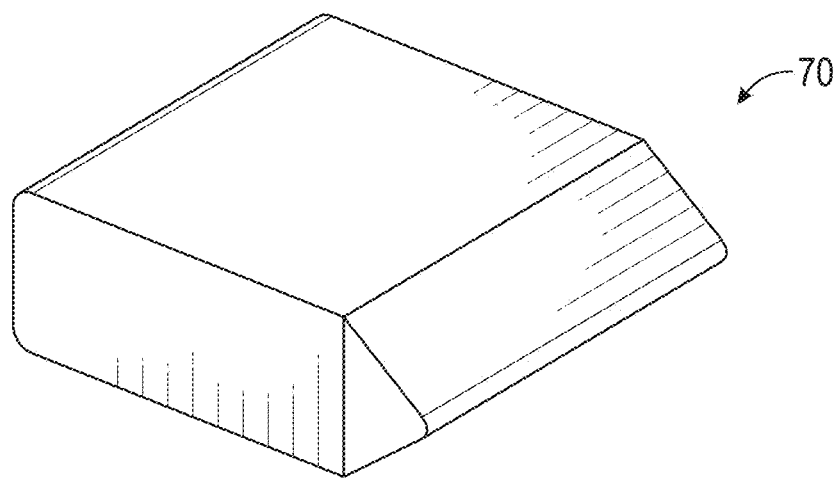
FIG. 7 illustrates an exemplary SI joint implant.

FIG. 7 illustrates an exemplary implant 70 or broach 70 with a sharpened distal end. If used as a broach, the broach 70 may be configured with any of the guide members herein, and in methods of use can be guided over one or more guides (before the implant is implanted) to create a space across the SI joint for the implant. The broach can be removed, and an implant can then be advanced over the guides, which is described in more detail below.

If used as an implant, the implant 70 may be configured with any of the guide members herein (e.g., including a lumen), and in methods of use can be guided over one or more guides to position the implant. The sharpened region of the implant may create the space as well as function as the implant.

Figure 8:
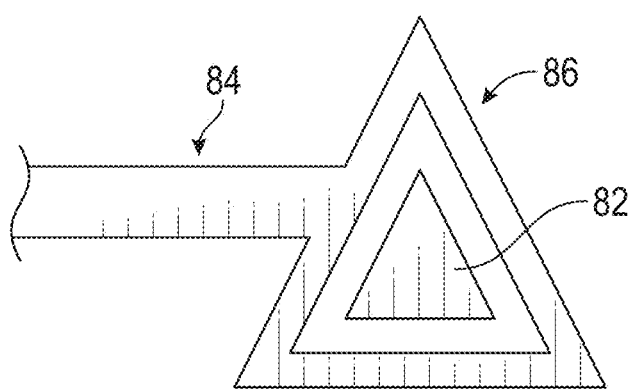
FIG. 8 illustrates a portion of an exemplary SI joint implant engaged with a positioning guide.

FIG. 8 illustrates an exemplary implant 84 that includes guide interface member 86, which is configured to interface with guide 82. In this exemplary embodiment, guide 82 has a triangular configuration (which may have other rectilinear configurations), and member 86 includes an inner surface triangular configuration (which may have other rectilinear configurations), as shown. Implant 84 may also have any number of members 86, each of which can be configured to interface with a different guide.

Any of the implants herein may also have a guide interface member with a first configuration and a second guide interface member with a second configuration different than the first. For example, any of the implants herein may have one or more interface members the same or similar to member 23, the same or similar to member 33, the same or similar to member 63, and/or the same or similar to members 86.

Figure 9:
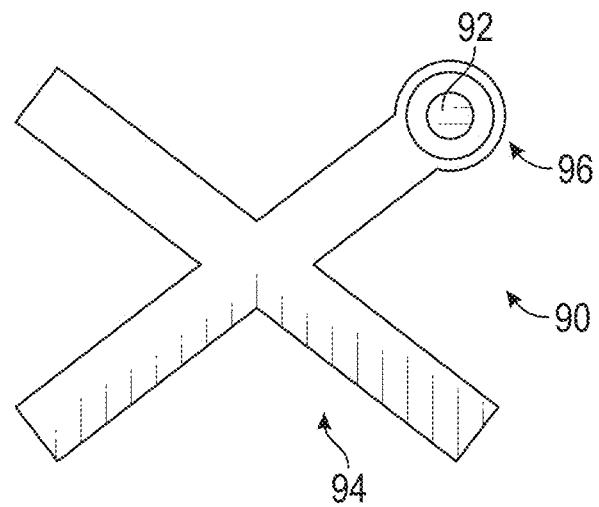
FIG. 9 illustrates a portion of an exemplary SI joint implant engaged with a positioning guide.

FIG. 9 illustrates an exemplary system 90 that includes implant 94. Implant 94 has a plurality of arms, and not all of the arms include a guide interface member at the respective arm end. In this embodiment only one of the arms has a guide interface member (in this embodiment member 96), but in other embodiments the implant may have any number of members less than the number of arms extending from a main body portion (e.g., two, three, four, etc.)

Figure 10:
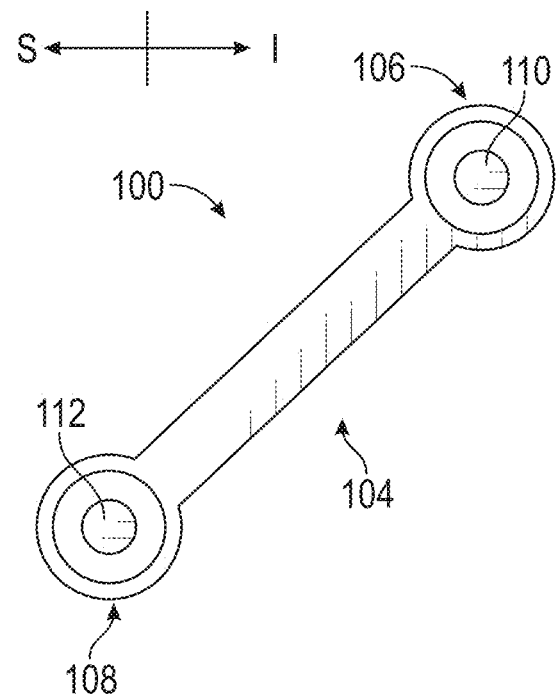
FIG. 10 illustrates an exemplary SI joint implant engaged with a plurality of positioning guides.

FIG. 10 illustrates an exemplary system 100 that includes an implant 104 (shown in end view) that includes ilium guide interface member 106 and sacrum guide interface member 108, each of which is configured to interface with guides 110 and 112, respectively. The position shown illustrates an as-implanted positioned across a SI joint, illustrating that any of the implants herein may be implanted with one guide member in one type of bone (e.g., 106) superior to another guide member in a different type of bone (e.g., ilium versus sacrum). For example, guide 110 may be positioned in iliac bone, and guide 112 may be positioned in a sacrum, either inferior to guide 110 as shown, or in other embodiments superior to guide 110, which is not shown, but which would be above guide 110 in FIG. 10.

Any of the implants herein may have one or more surfaces that are configured and adapted to facilitate at least one of bony ingrowth and ongrowth. For example, without limitation, any of the implants herein may include one or more of fenestrations, apertures, porous surfaces, irregular surfaces, etc., such as any that may be described in U.S. Pat. No. 9,044,321, U.S. Published Application 2013/0296953, U.S. Pat. Nos. 9,662,157, 10,166,033, U.S. Published Application 2016/0287171, the disclosures of which are incorporated by reference herein for all purposes.

As is set forth herein, SI joint implants herein may include one or more interface members, which may be configured as lumens or bores. The interface members are generally sized and configured to accommodate passage of one or more guides (such as an ilium guide), which are positioned within one or more of an ilium or a sacrum. In this way, the SI joint implants may be guided by the positioning guides to the intended implantation location across the SI joint without migrating (or at least minimizing migration) away from the denser iliac bone.

In some embodiments, the SI joint implants may include interface members in opposing sides or side regions of the SI joint implant, an example of which is shown in FIGS. 2A and 2B. In this arrangement, the implant is advanced over the guides to position the implant across the SI joint. The guides may be removed after the SI joint implant is delivered to its desired position, leaving the implant implanted across the SI joint.

One aspect of the disclosure is related to methods of positioning a SI joint stabilization implant across a SI joint from a dorsal approach. In these methods, the SI joint implant may be any of the SI joint implants herein. The methods may include advancing an elongate ilium positioning guide from a dorsal starting point, such as starting point 1122 shown in FIG. 11A, and into an ilium of a subject. For example only, FIGS. 2A and 2B illustrate exemplary ilium guide 22, but other types of ilium guides may be positioned from a dorsal approach into an ilium of the subject. FIG. 11A also illustrates a general region 1120 into which any of the ilium guides herein may be started and advanced into an ilium to function as a guide for the SI joint implant. The methods herein may include engaging a guide interface member of the SI joint implant with a positioning guide to restrict movement of the implant with respect to the positioning guide in at least one direction. For example only, FIGS. 1A and 1B illustrate ilium guide interface member 18 of SI joint implant 14, but other interface members herein may be engaged with any of the guides herein to restrict movement of the SI joint implant with respect to the positioning guide in at least one direction. The methods may include, at a time subsequent to the engaging step, advancing the implant across the SI joint while guiding the implant with the positioning guide to implant the implant across the SI joint. The methods further include removing the positioning guide from the ilium and leaving the implant implanted across the SI joint. The methods may include advancing a positioning guide into an ilium between lateral and medial cortical walls of the ilium, descriptions and locations of which are generally known and shown generally in FIGS. 11A and 11B. In these methods, engaging the implant with an ilium positioning guide helps maintain the implantation trajectory and limits the extent to which the implant migrates towards the sacrum while advancing the implant across the SI joint.

Some methods may also include advancing a sacrum positioning guide into a sacrum of the patient, and further engaging a second guide interface member of the implant with the sacrum positioning guide. In these examples, the implant advancing step may occur while also guiding the implant with the sacrum positioning guide. In these examples, the method also includes removing the sacrum positioning guide from the sacrum. Any of the methods herein may include positioning a sacrum positioning guide into a sacrum before or after an ilium positioning guide is positioned in an ilium.

In some methods, prior to implanting the implant, a sharpened broach may be guided over any of the positioning guides herein and advanced towards the SI joint to create a space for the SI joint implant while guiding the broach with the positioning guide. In these examples, the methods include removing the broach to allow dorsal access to the space. The implant may then be advanced over one or more positioning guides as described elsewhere herein.

Depending on the implant being implanted across the SI joint, any of the methods herein may also include positioning a second ilium positioning guide from a dorsal approach into the ilium of a subject. These examples may also include engaging a second guide interface member of the implant with the second ilium positioning guide to further restrict movement of the implant with respect to the second ilium positioning guide in at least one direction.

Depending on the implant being implanted across the SI joint, any of the methods herein may include positioning first and second sacral positioning guides from a dorsal approach into the sacrum of a subject. These examples may also include engaging first and second sacrum guide interface members of the implant with the first and second sacrum positioning guides to further restrict movement of the implant with respect to the first and second sacrum positioning guides in at least one direction.

Any of the individual method steps set forth herein may be combined with any other suitable method step or sequence of steps, unless the disclosure herein indicates to the contrary.

What is claimed is:

1. A method of positioning a sacroiliac ("SI") joint stabilization implant across a SI joint from a dorsal approach, comprising:
    advancing an elongate implant positioning guide ("positioning guide") in a dorsal trajectory into an ilium of a subject;
    positioning a SI joint stabilization implant lumen about the positioning guide to restrict movement of the implant with respect to the positioning guide in at least one direction;
    at a time subsequent to the positioning step, advancing the implant across the SI joint while guiding the implant with the positioning guide; and
    removing the positioning guide from the ilium and from within the SI joint stabilization implant lumen.

2. The method of claim 1, wherein advancing the positioning guide into the ilium comprises advancing the positioning guide into the ilium between lateral and medial cortical walls of the ilium.

3. The method of claim 2, further comprising viewing a radiographic teardrop view image that shows a teardrop region of the ilium of the subject to help guide the positioning guide into the ilium between the lateral and medial cortical walls of the ilium.

4. The method of claim 1, wherein advancing the positioning guide comprises advancing the positioning guide only into the ilium.

5. The method of claim 1, further comprising:
at a time subsequent to positioning the positioning guide into the ilium, advancing a sacrum positioning guide into a sacrum of the subject;
positioning an implant second lumen about the sacrum positioning guide, wherein the implant advancing step occurs while also guiding the implant with the sacrum positioning guide; and
removing the sacrum positioning guide from the sacrum.

6. The method of claim 5, wherein positioning an implant second lumen about the sacrum positioning guide occurs prior to advancing the sacrum positioning guide into the sacrum of the subject.

7. The method of claim 5, further comprising advancing a second sacrum positioning guide in a dorsal trajectory into the sacrum of a subject; and positioning a second sacrum lumen of the implant about the second sacrum positioning guide to restrict movement of the implant with respect to the second sacrum positioning guide in at least one direction.

8. The method of claim 1, wherein the positioning step limits the amount of implant migration towards a sacrum while advancing the implant across the SI joint.

9. The method of claim 1, further comprising, at a time prior to positioning the SI joint stabilization implant lumen about the positioning guide, engaging a sharpened broach with the positioning guide, and advancing the broach towards the SI joint to create a space for the implant while guiding the broach with the positioning guide; and removing the broach to allow dorsal access to the space.

10. The method of claim 1, wherein the implant has a sharpened front section, and wherein advancing the implant into the SI joint comprises advancing the sharpened front section through bone.

11. The method of claim 1, wherein positioning the SI joint stabilization implant lumen about the positioning guide comprises positioning an annular member of the implant lumen over a proximal region of the positioning guide.

12. The method of claim 1, wherein positioning the SI joint stabilization implant lumen about the positioning guide comprises positioning an arcuate member of the implant lumen around a proximal region of the positioning guide.

13. The method of claim 1, further comprising advancing a second ilium positioning guide in a dorsal trajectory into the ilium of a subject; and positioning a second lumen of the implant about the second ilium positioning guide to restrict movement of the implant with respect to the second ilium positioning guide in at least one direction.

14. A method of positioning a sacroiliac ("SI") joint stabilization implant across a SI joint from a dorsal approach, comprising:
advancing an elongate ilium positioning guide in a dorsal trajectory into an ilium of a subject;
advancing an elongate sacrum positioning guide in a dorsal trajectory into a sacrum of the subject;
positioning a SI joint stabilization implant lumen about the ilium positioning guide to restrict movement of the implant with respect to the ilium positioning guide in at least one direction;
positioning a SI joint stabilization implant second lumen about the sacrum positioning guide to restrict movement of the implant with respect to the sacrum positioning guide in at least one direction;
at a time subsequent to the positioning steps, advancing the implant across the SI joint while guiding the implant with the ilium positioning guide and with the sacrum positioning guide;
removing the ilium positioning guide from the ilium and from within the SI joint stabilization implant lumen; and
removing the sacrum positioning guide from the ilium and from within the SI joint stabilization implant second lumen.

15. The method of claim 14, wherein advancing the elongate ilium positioning guide occurs prior in time to advancing the elongate sacrum positioning guide.

16. The method of claim 14, wherein advancing the elongate ilium positioning guide occurs subsequent in time to advancing the elongate sacrum positioning guide.

17. The method of claim 14, wherein advancing the ilium positioning guide into the ilium comprises advancing the positioning guide into the ilium between lateral and medial cortical walls of the ilium.

18. The method of claim 14, wherein positioning a SI joint stabilization implant second lumen about the sacrum positioning guide occurs prior in time to advancing the sacrum positioning guide into the sacrum of the subject.

19. The method of claim 14, wherein positioning a SI joint stabilization implant lumen about the ilium positioning guide occurs prior in time to advancing the ilium positioning guide into the ilium of the subject.

20. The method of claim 14, further comprising advancing a second sacrum positioning guide from a dorsal approach into the sacrum of a subject, and engaging a second sacrum lumen of the implant about the second sacrum positioning guide to restrict movement of the implant with respect to the second sacrum positioning guide in at least one direction.

21. The method of claim 14, wherein positioning a SI joint stabilization implant lumen about the ilium positioning guide comprises positioning an annular positioning guide interface member of the implant over a proximal region of the ilium positioning guide.

22. The method of claim 14, wherein positioning a SI joint stabilization implant second lumen about the sacrum positioning guide comprises positioning an annular sacrum positioning guide interface member of the implant over a proximal region of the sacrum positioning guide.

* * * * *